US010974233B2

(12) United States Patent
Hu et al.

(10) Patent No.: US 10,974,233 B2
(45) Date of Patent: Apr. 13, 2021

(54) CATALYST FOR PREPARING 1,5-PENTANEDIOL VIA HYDROGENOLYSIS OF TETRAHYDROFURFURYL ALCOHOL, METHOD AND APPLICATION THEREOF

(71) Applicant: WANHUA CHEMICAL GROUP CO., LTD., Shandong (CN)

(72) Inventors: Jianglin Hu, Shandong (CN); Yunhai Liu, Shandong (CN); Yuan Li, Shandong (CN); Qingmei Jiang, Shandong (CN); Yanfang Song, Shandong (CN); Yang Yang, Shandong (CN); Changsheng Chen, Shandong (CN); Ke Ding, Shandong (CN); Wei Zeng, Shandong (CN); Hengdong Yang, Shandong (CN); Kun Wang, Shandong (CN); Weiqi Hua, Shandong (CN)

(73) Assignee: WANHUA CHEMICAL GROUP CO., LTD., Yantai (CN)

( * ) Notice: Subject to any disclaimer, the term of this patent is extended or adjusted under 35 U.S.C. 154(b) by 0 days.

(21) Appl. No.: 16/489,599

(22) PCT Filed: Mar. 27, 2017

(86) PCT No.: PCT/CN2017/078264
§ 371 (c)(1),
(2) Date: Aug. 28, 2019

(87) PCT Pub. No.: WO2018/170932
PCT Pub. Date: Sep. 27, 2018

(65) Prior Publication Data
US 2020/0009544 A1 Jan. 9, 2020

(30) Foreign Application Priority Data
Mar. 23, 2017 (CN) .......................... 201710177295.3

(51) Int. Cl.
B01J 31/06 (2006.01)
C07C 29/132 (2006.01)
B01J 23/14 (2006.01)
B01J 23/20 (2006.01)
B01J 23/22 (2006.01)
(Continued)

(52) U.S. Cl.
CPC ............... *B01J 31/06* (2013.01); *B01J 23/14* (2013.01); *B01J 23/20* (2013.01); *B01J 23/22* (2013.01); *B01J 23/28* (2013.01); *B01J 23/30* (2013.01); *B01J 23/34* (2013.01); *B01J 23/36* (2013.01); *B01J 23/42* (2013.01); *B01J 23/44* (2013.01); *B01J 23/462* (2013.01); *B01J 23/464* (2013.01); *B01J 23/468* (2013.01); *B01J 23/52* (2013.01); *B01J 23/626* (2013.01); *B01J 23/6482* (2013.01); *B01J 23/6484* (2013.01); *B01J 23/6486* (2013.01); *B01J 23/6527* (2013.01); *B01J 23/6562* (2013.01); *B01J 23/6567* (2013.01); *B01J 31/069* (2013.01); *B01J 31/1616* (2013.01); *B01J 31/1633* (2013.01); *B01J 31/1658* (2013.01); *B01J 31/181* (2013.01); *B01J 31/183* (2013.01); *B01J 31/1815* (2013.01); *B01J 37/0209* (2013.01); *C07C 29/132* (2013.01); *B01J 2231/48* (2013.01); *B01J 2231/641* (2013.01); *B01J 2531/18* (2013.01); *B01J 2531/42* (2013.01); *B01J 2531/56* (2013.01); *B01J 2531/57* (2013.01); *B01J 2531/58* (2013.01); *B01J 2531/64* (2013.01); *B01J 2531/66* (2013.01);
(Continued)

(58) Field of Classification Search
None
See application file for complete search history.

(56) References Cited

U.S. PATENT DOCUMENTS
2014/0243562 A1  8/2014  Omeis et al.

FOREIGN PATENT DOCUMENTS
CN    1565728 A     1/2005
CN    101225022 A   7/2008
(Continued)

OTHER PUBLICATIONS

Sulman, E. M. et al. "Kinetics of phenol hydrogenation over Pd-containing hypercrosslinked polystyrene" Chemical Engineering Journal 176-177 (2011) 33-41 (Year: 2011).*
Guan, J. et al. "Role of MoO3 on a Rhodium Catalyst in the Selective Hydrogenolysis of Biomass-Derived Tetrahydrofurfuryl Alcohol into 1,5-Pentanediol" J. Phys. Chem. C 2014, 118, 25555-25566 (Year: 2014).*
Purolite "Macronet MN270" 2020 (Year: 2020).*
First Search Report for CN Application No. 201710177295.3, dated Aug. 8, 2019, 4 pages.
(Continued)

Primary Examiner — Medhanit W Bahta
(74) Attorney, Agent, or Firm — Armstrong Teasdale LLP

(57) ABSTRACT

The present invention provides a method for preparing 1,5-pentanediol via hydrogenolysis of tetrahydrofurfuryl alcohol. The catalyst used in the method is prepared by supporting a noble metal and a promoter on an organic polymer supporter or an inorganic hybrid material supporter, wherein the supporter is functionalized by a nitrogen-containing ligand. When the catalyst is used in the hydrogenolysis of tetrahydrofurfuryl alcohol to prepare 1,5-pentanediol, a good reaction activity and a high selectivity can be achieved. The promoter and the nitrogen-containing ligand in the supporter are bound to the catalyst through coordination, thereby the loss of the promoter is significantly decreased, and the catalyst has a particularly high stability. The lifetime investigation of the catalyst, which has been reused many times or used continuously for a long term, suggests that the catalyst has no obvious change in performance, thus reducing the overall process production cost.

15 Claims, No Drawings

(51) Int. Cl.
- *B01J 23/28* (2006.01)
- *B01J 23/30* (2006.01)
- *B01J 23/34* (2006.01)
- *B01J 23/36* (2006.01)
- *B01J 23/42* (2006.01)
- *B01J 23/44* (2006.01)
- *B01J 23/46* (2006.01)
- *B01J 23/52* (2006.01)
- *B01J 31/16* (2006.01)
- *B01J 23/652* (2006.01)
- *B01J 31/18* (2006.01)
- *B01J 23/648* (2006.01)
- *B01J 23/656* (2006.01)
- *B01J 37/02* (2006.01)
- *B01J 23/62* (2006.01)

(52) U.S. Cl.
CPC ........ *B01J 2531/72* (2013.01); *B01J 2531/74* (2013.01); *B01J 2531/82* (2013.01)

(56) References Cited

FOREIGN PATENT DOCUMENTS

| | | | |
|---|---|---|---|
| CN | 101270032 | A | 9/2008 |
| CN | 101481444 | A | 7/2009 |
| CN | 101745408 | A | 6/2010 |
| CN | 101851307 | A | 10/2010 |
| CN | 102134180 | A | 7/2011 |
| CN | 102320923 | A | 1/2012 |
| CN | 102872897 | A | 1/2013 |
| CN | 102911011 | A | 2/2013 |
| CN | 102942448 | A | 2/2013 |
| CN | 103071512 | A | 5/2013 |
| CN | 103848719 | A | 6/2014 |
| CN | 104016831 | A | 9/2014 |
| CN | 104513338 | A | 4/2015 |
| JP | S61130249 | A | 6/1986 |

OTHER PUBLICATIONS

First Office Action for CN Application No. 201710177295.3 and partial English translation, dated Aug. 16, 2019, 4 pages.

Wang, Z. et al. 2014. Chemoselective hydrogenolysis of tetrahydrofurfuryl alcohol to 1,5-pentanediol over Ir-MoOx/SiO2 catalyst. Journal of Energy Chemistry 23(4):427-434. Abstract.

English translation of International Search Report for International Application No. PCT/CN2017/078264, dated Dec. 29, 2017, 2 pages.

Adkins, H., Conner, R. 1931. The Catalytic Hydrogenation of Organic Compounds Over Copper Chromite. J. Am. Chem. Soc., 153(3):1091-1095. First page.

Koso, S. et al. 2009. Chemoselective hydrogenolysis of tetrahydrofurfuryl alcohol to 1,5-pentanediol. Chem. Comm., 45(15):2035-2037. Abstract.

Koso, S. et al. 2009. Promoting effect of Mo on the hydrogenolysis of tetrahydrofurfuryl alcohol to 1,5-pentanediol over Rh/SiO2. J. Catal., 267:89-92. Abstract.

Xu, W. et al. 2011. Direct catalytic conversion of furfural to 1,5-pentanediol by hydrogenolysis of the furan ring under mild conditions over Pt/Co AlO catalyst. Chem. Comm., 47(13):3924-3926. Abstract.

Chen, K. et al. 2012. C—O bond hydrogenolysis of cyclic ethers with OH groups over rhenium-modified supported iridium catalysts. J. Catal., 294:171-183. Abstract.

Extended European Search Report for EP Application 17902164.7 dated Dec. 10, 2020; 9 pp.

Bilodeau, Mark T., "Solid-Supported Synthesis of Imadazoles: A Strategy for Direct Resin-Attachment to the Imidazole Core", J. Org. Chem., 1998, vol. 63; pp. 2800-2801.

Sofia, L.T. Aany et al., "Immobilization of Phosphotungstic Acid (PTA) on Imidazole Functionalized Silica: Evidence for the Nature of PTA Binding by Solid State NMR and Reaction Studies", J. Phys. Chem., published on the internet Nov. 16, 2009, pp. 21114-21122.

* cited by examiner

CATALYST FOR PREPARING 1,5-PENTANEDIOL VIA HYDROGENOLYSIS OF TETRAHYDROFURFURYL ALCOHOL, METHOD AND APPLICATION THEREOF

CROSS-REFERENCE TO RELATED APPLICATIONS

This application is a U.S. National Phase Application of PCT/CN2017/078264, filed Mar. 27, 2017, which claims the benefit of priority to CN Application No. 201710177295.3, filed Mar. 23, 2017, the contents of which are hereby expressly incorporated by reference in their entirety.

TECHNICAL FIELD

The present invention relates to the fields of catalyst technology and organic synthesis, and more specifically, relates to the preparation of the supported catalyst using a supporter that is functionalized by a nitrogen-containing ligand, and the method for preparing 1,5-pentanediol by hydrogenolysis of a biomass derivative tetrahydrofurfuryl alcohol.

BACKGROUND OF ART 1,5-pentanediol is a dihydric primary alcohol with an odd number of carbon atoms. It is mainly used in the production of polyester polyols, esters used for synthesizing lubricants, polyurethane foam plastics, elastomer, plasticizers, saturated/unsaturated polyester resins, powder coatings, inks, perfumes, etc.

Patent CN1565728 discloses a process for preparing 1,5-pentanediol by hydrogenation reaction of dimethyl glutarate used as a raw material, under the action of copper-zinc-aluminium catalyst. Patent CN102320923 discloses a method for preparing the product 1,5-pentanediol. The method includes refining and separating a dibasic ester to obtain dimethyl succinate, dimethyl glutarate and dimethyl adipate, preparing a crude product of 1,5-pentanediol by the hydrogenation reaction of dimethyl glutarate and hydrogen in a hydrogenation reactor, and decolorizing and filtering the crude product to obtain the product 1,5-pentanediol. In this method, the dimethyl glutarate is derived primarily from the esterification of glutaric acid which is a by-product of the preparation of adipic acid. Thus, it's limited not only by the adipic acid industry and the lack of sources, but also by the need for a lengthy process which includes several steps, comprising distillation, purification, hydrogenation, separation and refinement, etc.

Patents CN101225022 and CN101270032 disclose using supported Ni catalyst and supported Ru catalyst, respectively, for catalyzing the hydrogenation reaction of glutaraldehyde to 1,5-pentanediol. Currently, the glutaraldehyde is obtained by the catalyzed condensation reaction of vinyl ether and propenal followed by hydrolysis. Vinyl ether is very unstable and extremely explosive, and has a high security risk. In addition, glutaraldehyde as a raw material is not resourceful and its price is high.

The biomass derivative furfural can be prepared from agricultural wastes such as corn cob, bagasse, etc., which are produced in large quantities in North China and Shandong Province and have advantages such as wide variety of sources, large reserves, etc. Using furfural and its derivatives as raw materials in the synthesis of various chemicals is low in cost and environmental friendly, and it's gaining more and more attention. In recent years, a lot of studies have been carried out on the route of preparing 1,5-pentanediol by the catalytic hydrogenolysis of furfural, furfuryl alcohol and tetrahydrofurfuryl alcohol that are cheap. They are specifically described as follows:

1) Furfural is preliminary hydrogenated to obtain furfuryl alcohol. After that, the furfuryl alcohol was hydrotreated by using copper chromite as a catalyst under high-temperature and high-pressure conditions (175° C., 10-15 MPa), and the reaction has a lower yield of about 30% for 1,5-pentanediol (J. Am. Chem. Soc., 1931, 53, 1091). The research group of Lu Guanzhong successfully developed a method for preparing 1,5-pentanediol via catalytic hydrogenation under mild conditions (140° C., 1.5 MPa), using furfural as a raw material and Pt/$Co_2AlO_4$ as a catalyst, and after 24 h of reaction, 1,5-pentanediol was obtained with a yield of less than 40% and complex by-products (Chem. Comm., 2011, 47, 3924-3926 and CN102134180). Patent CN102872897 discloses preparing 1,5-pentanediol by using a hydrogen-type ultrastable Y molecular sieve (H-USY) supported Pt catalyst and using hydrochloric acid as a promoter in the reaction, and the reaction is carried out at 120° C. and 1.5 MPa; though 1,5-pentanediol is obtained with a yield of up to 82.6% after 24 h of reaction, the activity of the catalyst is still not high enough and the present of hydrochloric acid causes serious corrosion problems.

2) Tetrahydrofurfulyl alcohol can be obtained by complete hydrogenation. It's disclosed in earlier documents that the synthesis of 1,5-pentanediol from tetrahydrofurfuryl alcohol requires three steps: firstly, producing dihydropyran from tetrahydrofurfuryl alcohol under the action of $Al_2O_3$; then, hydrolyzing the dihydropyran to give 5-hydroxylvaleraldehyde; finally, hydrogenating the 5-hydroxylvaleraldehyde by using a copper chromite catalyst. The problem of low product selectivity is overcome by this method, but it requires separation and purification in each step, thus adding complexity to the reaction step (J. Am. Chem. Soc., 1946, 68, 1646). It is first reported by the Japanese Tomishige research team that, in the preparation of 1,5-pentanediol via the one-step hydrogenolysis of tetrahydrofurfuryl alcohol, which is carried out in a batch tank reactor under conditions of 120° C. and 8 MPa, a conversion rate of at least 90% and a selectivity up to 90% for 1,5-pentanediol can be achieved after a 24 h reaction time, using tetrahydrofurfuryl alcohol as a raw material, and using Rh/$SiO_2$ catalyst or Ir/$SiO_2$ catalyst that is promoted by Re, Mo or W. However, the catalyst activity is significantly decreased in the process of reusing the catalyst. The conversion rate reaches 79% for the first use of the catalyst, while it is decreased to 64.5% for the fifth use of the catalyst (Chem. Commum., 2009, 45, 2035-2037, J. Catal., 2009, 267, 89-92, J. Catal., 2012, 294, 171-183). Patent CN103848719 discloses that Ir/$SiO_2$ catalyst promoted by V, Nb or Ta has activity on the one-step hydrogenolysis of tetrahydrofurfuryl alcohol to produce 1,5-pentanediol; the conversion rate is not higher than 60% with the selectivity of about 90% for 1,5-pentanediol, under the reaction conditions of 80° C. and 6 MPa in a fixed bed reactor. Compared with the above described process routes, the process route of preparing 1,5-pentanediol by the one-step hydrogenolysis of tetrahydrofurfuryl alcohol is simple, and the conversion rate of raw material and the selectivity of the target product 1,5-pentanediol are high. The shortages of this process route are that the catalyst activity is still not high enough, and the promoter (Re, Mo or W, etc.) is lost during use, resulting in catalyst deactivation. Thus, the catalyst can't be reused for many times or used continuously for a long time, and the production cost of the whole process is too high. Patent CN103071512 uses Raney Co or Cu catalyst, which was promoted by Re, Mo or W, in the one-step hydrogenolysis of tetrahydrofurfuryl alcohol to produce 1,5-pentanediol; although no noble metal is used, the performance of the catalyst is poor; after 24 h of reaction in a batch reactor at 120° C. and 8 MPa, the conversion rate is not higher than 10% and the selectivity for 1,5-pentanediol is 46.7%.

SUMMARY OF THE PRESENT INVENTION

The present invention provides a catalyst for preparing 1,5-pentanediol via hydrogenolysis of tetrahydrofurfuryl alcohol, a preparation method and a using method thereof. The catalysts in the specific examples of the present invention have the characteristics of good stability and long service life, and exhibit high activity and selectivity in the hydrogenolysis reaction of tetrahydrofurfuryl alcohol for preparing 1,5-pentanediol.

The present invention adopts the following technical solutions:

A catalyst used for preparing 1,5-pentanediol by hydrogenolysis of tetrahydrofurfuryl alcohol, said catalyst comprises a supporter, an active component supported on the supporter, and a promoter supported on the supporter; wherein, the supporter is a polystyrene grafted with a nitrogen-containing ligand or a silica gel grafted with a nitrogen-containing ligand; said active component is any one or more of metal elements Rh, Ir, Pt, Pd, Ru, Au, etc.; said promoter is any one or more of metal elements Re, Mo, W, V, Nb, Ta, Mn, Sn, etc. The nitrogen-containing ligand in said polystyrene grafted with a nitrogen-containing ligand is any one of imidazole, pyridine, bipyridine and 1,10-phenanthroline; the nitrogen-containing ligand in said silica gel grafted with a nitrogen-containing ligand is any one of imidazole, pyridine, bipyridine and 1,10-phenanthroline. Based on the total weight of the catalyst, said active component is supported in an amount of 0.05-10 wt %, preferably 1-5 wt %; the molar ratio of the active component, the promoter and the nitrogen-containing ligand is 1:(0.01-2):(0.05-4), preferably 1:(0.05-1):(0.1-2).

Preferably, said polystyrene grafted with a nitrogen-containing ligand has the following structural formula:

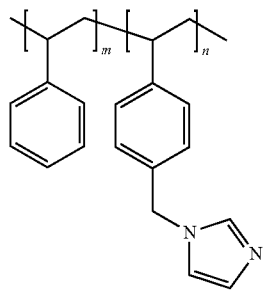
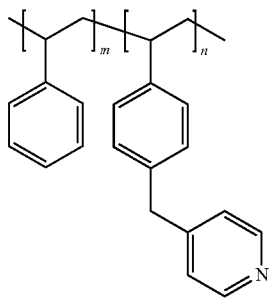

-continued

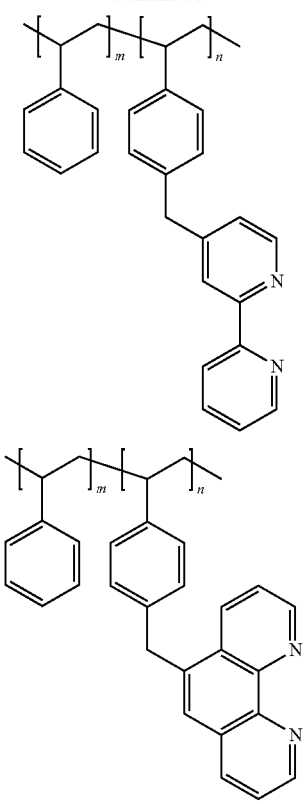

Wherein, m=500~2,000, n=200~1,000, preferably m=800~1500, n=300~800.

Preferably, said silica gel grafted with a nitrogen-containing ligand has the following structural formula:

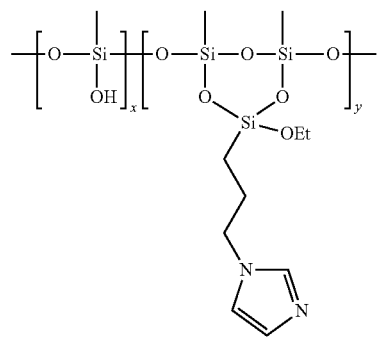

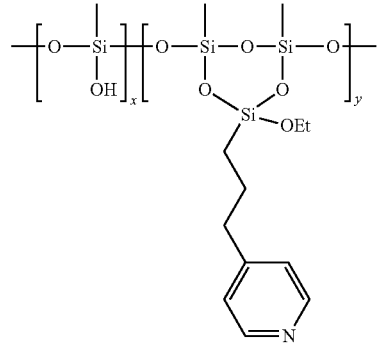

-continued

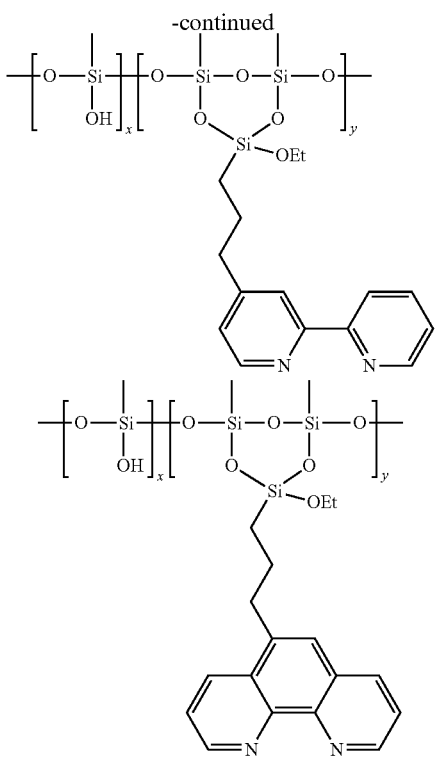

Wherein, x=5,000~10,000, y=200~1,000, preferably x=6,000~8,000, y=300~800.

A method for preparing the catalyst, wherein the supporter is added into a soluble salt solution of the active component for isometric impregnation, and then dried at 80~120° C. for 6~24 hours; a soluble salt solution of the promoter is further used for isometric impregnation, and the impregnated supporter is then dried at 80~120° C. for 6~24 hours to obtain the catalyst.

The soluble salt of the active component is selected from one or more of rhodium chloride, chloroiridic acid, chloroplatinic acid, palladium chloride, ruthenium chloride and chloroauric acid; the soluble salt of the promoter is selected from one or more of ammonium rhenate, ammonium molybdate, ammonium metatungstate, ammonium vanadate, niobiumtartrate, tantalumtartrate, manganese acetate and stannic chloride.

A method for preparing 1,5-pentanediol by hydrogenolysis of tetrahydrofurfuryl alcohol using the catalyst, wherein the catalyst, before use, needs to be reduced in situ in the presence of hydrogen to have catalytic activity, and the reduction condition is as follows: the hydrogen pressure is 0.1~1 MPa, preferably 0.2~0.4 MPa; for each 100 g of the hydrogenolysis catalyst, the $H_2$ flow rate is 0.2~10 L/min, preferably 1~5 L/min; the reduction temperature is 50~200° C., preferably 100~180° C.; and the reduction time is 1~10 hours, preferably 2~6 hours. When the reaction is carried out in a batch reactor, the mass concentration of the aqueous solution of tetrahydrofurfuryl alcohol is 5~100%; the amount of the catalyst used is 1~10 wt % of the mass of tetrahydrofurfuryl alcohol; the reaction temperature is 50~150° C., preferably 60~120° C.; the hydrogen pressure is 1~20 MPa (gauge pressure), preferably 2~10 MPa; the reaction time is 2~24 hours, preferably 2~6 hours. When the reaction is carried out in a fixed bed reactor, the concentration of the aqueous solution of tetrahydrofurfuryl alcohol is 5~100%; the reaction temperature is 50~150° C., preferably 60~120° C.; the hydrogen pressure is 1~20 MPa (gauge pressure), preferably 2~10 MPa; the mass space velocity of tetrahydrofurfuryl alcohol feed liquid/catalyst in the fixed bed reactor is 0.5~4 $h^{-1}$, preferably 1~3 $h^{-1}$; the volume space velocity of hydrogen/catalyst is 500~1500 $h^{-1}$, preferably 800~1200 $h^{-1}$.

Use of the catalyst in the method of preparing 1,5-pentanediol by the hydrogenolysis of tetrahydrofurfuryl alcohol.

The catalysts in the specific examples of the present invention have the following beneficial effects:

When the catalyst is used in the hydrogenolysis of tetrahydrofurfuryl alcohol to prepare 1,5-pentanediol, a good reaction activity and a high selectivity can be achieved. The promoter is bound to the catalyst through coordinating with the nitrogen-containing ligand in the supporter, thereby the loss of the promoter is significantly decreased and the stability of the catalyst is very well. The lifetime investigation of the catalyst, that has been reused many times or used continuously for a long term, suggests that the catalyst has no obvious change in performance, thus greatly reducing the overall process production cost.

DETAILED DESCRIPTION

The present invention will be further illustrated below with reference to examples, it should be noted that the examples are not the limitations for the scope of the present invention.

The raw material tetrahydrofurfuryl alcohol was purchased from Zibo Hua'ao Chemical Co., Ltd.; the soluble salts of the active component—hereinafter also referred to as the soluble salts of the noble metal M (rhodium chloride, chloroiridic acid, chloroplatinic acid, palladium chloride, ruthenium chloride, chloroauric acid), and the soluble salts of the promoter P (ammonium rhenate, ammonium molybdate, ammonium metatungstate, ammonium vanadate, ruthenium chloride, niobiumtartrate, tantalumtartrate, manganese acetate, stannic chloride) were purchased from Sinopharm Group Chemical Reagents Co., Ltd. The supporters S, i.e., a polystyrene and a silica gel that were grafted with a nitrogen-containing ligand (imidazole, pyridine, bipyridine, 1,10-phenanthroline), were purchased from Sigma-Aldrich Reagent Company (the product numbers were 549363 (m=1240, n=320), 192074 (m=960, n=400), 589993 (m=1070, n=530), 561878 (m=1150, n=670); 56760 (x=7300, y=390), 537985 (x=6500, y=460), 537950 (x=8000, y=710), 569798 (x=7100, y=650), respectively).

Their structural formulas are shown, respectively, as follows:

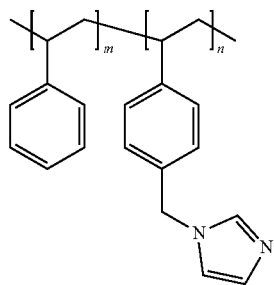

m = 1240, n = 320

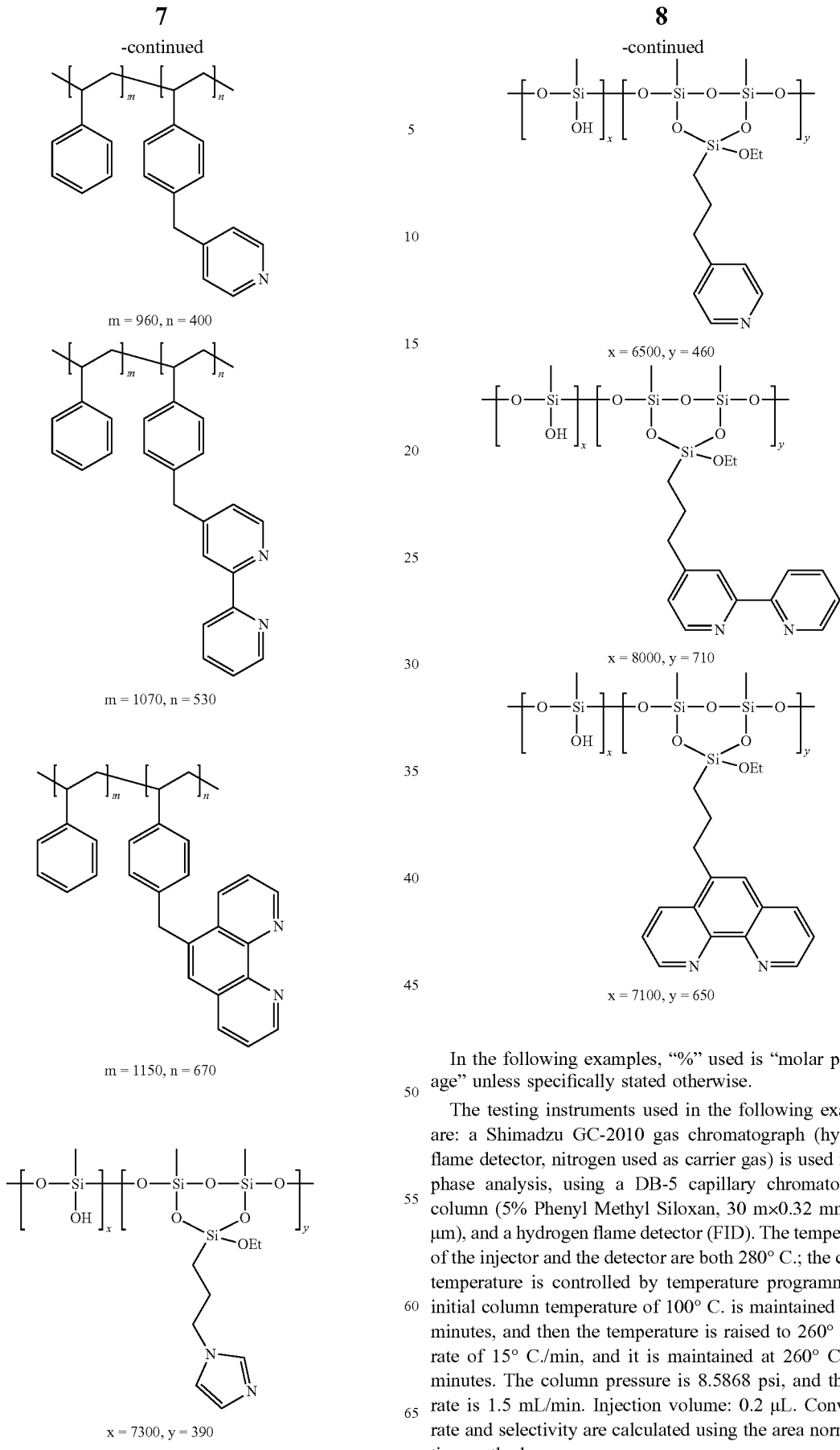

In the following examples, "%" used is "molar percentage" unless specifically stated otherwise.

The testing instruments used in the following examples are: a Shimadzu GC-2010 gas chromatograph (hydrogen flame detector, nitrogen used as carrier gas) is used for gas phase analysis, using a DB-5 capillary chromatography column (5% Phenyl Methyl Siloxan, 30 m×0.32 mm×0.25 μm), and a hydrogen flame detector (FID). The temperatures of the injector and the detector are both 280° C.; the column temperature is controlled by temperature programme: the initial column temperature of 100° C. is maintained for 0.5 minutes, and then the temperature is raised to 260° C. at a rate of 15° C./min, and it is maintained at 260° C. for 5 minutes. The column pressure is 8.5868 psi, and the flow rate is 1.5 mL/min. Injection volume: 0.2 μL. Conversion rate and selectivity are calculated using the area normalization method.

Examples 1~24: Catalyst Preparation

The preparation was carried out using isometric impregnation step by step. Firstly, soluble salts (rhodium chloride, chloroiridic acid, chloroplatinic acid, palladium chloride, ruthenium chloride, chloroauric acid) of noble metal M (Rh, Ir, Pt, Pd, Ru, Au) were separately prepared as aqueous solutions. Supporters S in powder were added into the above prepared aqueous solutions according to the ratios in Table 1, and the mixtures were stirred until homogeneously mixed. The supporters S were impregnated for 12 hours at room temperature, and then dried at 120° C. for 12 hours. Then, soluble salts (ammonium rhenate, ammonium molybdate, ammonium metatungstate, ammonium vanadate, niobiumtartrate, tantalumtartrate, manganese acetate, stannic chloride) of the promoter P (Re, Mo, W, V, Nb, Ta, Mn, Sn) were separately prepared as aqueous solutions; and they were added into the above impregnated supporters S which had been impregnated with noble metal M component, according to the ratios in Table 1; the mixture were stirred until homogenously mixed. After impregnated for 12 hours at room temperature, the impregnated supporters S were dried at 120° C. for 12 hours, obtaining catalysts with different content of active component.

Examples 28~54: Catalyst Evaluation—Batch Reactor

The catalyst evaluation of the present invention was carried out in a batch reactor, having a reactor volume of 5000 mL and made of stainless steel. A certain amount of catalyst was added into the reactor, and the catalyst was reduced in situ for 4 hours, at a reduction temperature of 150° C., a $H_2$ pressure of 0.3 MPa and a $H_2$ flow rate of 1.5 L/min. After the reduction, the temperature was lowered to the reaction temperature, and 3000 g of tetrahydrofurfuryl alcohol aqueous solution with a certain concentration was added; the temperature was adjusted to the reaction temperature, and hydrogen with a certain pressure was charged into the reactor to perform the reaction. The reaction was completed after a certain period of time. The specific reaction conditions were shown in Table 2. After the temperature was lowered and the pressure was released, a liquid sample was taken. The liquid sample was analyzed using the gas chromatograph equipped with a DB-5 capillary column and a flame ionization detector (FID) as described above.

The catalyst of the present invention was reused in the batch reactor. After the previous reaction in the reactor was completed, the reaction liquid was removed through a filter built in the reactor and the catalyst was left in it. 3000 g of aqueous solution of tetrahydrofurfuryl alcohol with a certain concentration was added again into the reactor, and the temperature was adjusted to the reaction temperature; hydro-

TABLE 1

Catalyst preparation

| Catalyst No. | Noble metal M | Promoter P | Supporter S | Content of M (wt %) | M:P:nitrogen-containing ligand (molar ratio) |
|---|---|---|---|---|---|
| 1# | Rh | Re | polystyrene grafted with imidazole | 5 | 1:0.5:0.5 |
| 2# | Rh | Mo | silica gel grafted with pyridine | 4 | 1:0.13:0.26 |
| 3# | Rh | W | polystyrene grafted with pyridine | 3 | 1:1:1.1 |
| 4# | Rh | V | silica gel grafted with 1,10-phenanthroline | 2 | 1:0.05:0.25 |
| 5# | Rh | Nb | polystyrene grafted with pyridine | 1 | 1:0.1:0.15 |
| 6# | Rh | Ta | silica gel grafted with bipyridine | 4.5 | 1:0.15:0.09 |
| 7# | Rh | Mn | polystyrene grafted with 1,10-phenanthroline | 3.5 | 1:0.2:0.14 |
| 8# | Rh | Sn | silica gel grafted with imidazole | 2.5 | 1:0.3:0.24 |
| 9# | Rh | Re | silica gel grafted with pyridine | 6.5 | 1:0.74:1.23 |
| 10# | Ir | Re | polystyrene grafted with pyridine | 4 | 1:0.4:0.36 |
| 11# | Ir | Mo | silica gel grafted with bipyridine | 3 | 1:0.6:0.72 |
| 12# | Ir | W | Polystyrene grafted with 1,10-phenanthroline | 4.3 | 1:0.7:0.91 |
| 13# | Ir | V | silica gel grafted with imidazole | 2.6 | 1:0.8:1.12 |
| 14# | Ir | Nb | polystyrene grafted with imidazole | 3 | 1:0.9:1.44 |
| 15# | Ir | Ta | silica gel grafted with pyridine | 1.8 | 1:0.22:0.37 |
| 16# | Ir | Mn | polystyrene grafted with bipyridine | 1.2 | 1:0.34:0.61 |
| 17# | Ir | Sn | silica gel grafted with 1,10-phenanthroline | 4.8 | 1:0.46:0.87 |
| 18# | Ir | Mo | polystyrene grafted with imidazole | 8.9 | 1:0.86:1.39 |
| 19# | Pt | Re | silica gel grafted with imidazole | 4.1 | 1:0.58:0.29 |
| 20# | Pt | Mo | polystyrene grafted with 1,10-phenanthroline | 2.5 | 1:0.63:0.63 |
| 21# | Pd | W | silica gel grafted with bipyridine | 3.7 | 1:0.75:1.5 |
| 22# | Pd | V | polystyrene grafted with pyridine | 4.4 | 1:0.87:0.87 |
| 23# | Ru | Nb | polystyrene grafted with imidazole | 2.3 | 1:0.99:1 |
| 24# | Ru | Ta | silica gel grafted with 1,10-phenanthroline | 1.7 | 1:0.81:0.9 |
| 25# | Au | Mn | polystyrene grafted with bipyridine | 2.8 | 1:0.73:0.7 |
| 26# | Au | Sn | silica gel grafted with pyridine | 3.9 | 1:0.55:1 |
| 27# | Au | W | silica gel grafted with bipyridine | 9.5 | 1:0.91:1.98 | gen with a certain pressure was charged into the reactor to perform the reaction. The reaction was completed after a certain period of time. The specific conditions were the same as those in the previous reaction.

pipe having an external diameter of 40 mm, an internal diameter of 20 mm and a length of 1000 mm. 50 g of the catalyst was loaded into the reactor. Before the reaction, the loaded catalyst was reduced in situ for 4 hours, at a reduction

TABLE 2

Reaction conditions and results in the batch reactor

| Examples | Catalyst | The amount of catalyst (wt %) | The concentration of tetrahydrofurfuryl alcohol (wt %) | Temperature (° C.) | Hydrogen pressure (MPa) | Time (h) | The first use Conversion rate (%) | Selectivity (%) | The 10th reuse Conversion rate (%) | Selectivity (%) |
|---|---|---|---|---|---|---|---|---|---|---|
| 28 | 1# | 6 | 50 | 100 | 5.5 | 2.5 | 95.2 | 95.0 | 94.5 | 95.3 |
| 29 | 2# | 7 | 60 | 95 | 6 | 3 | 93.7 | 94.3 | 93.0 | 94.7 |
| 30 | 3# | 5 | 40 | 100 | 4.5 | 4 | 94.5 | 91.8 | 94.7 | 91.8 |
| 31 | 4# | 4 | 20 | 105 | 8 | 3.5 | 95.3 | 96.0 | 95.2 | 96.1 |
| 32 | 5# | 3 | 70 | 120 | 7 | 4 | 92.4 | 95.3 | 92.5 | 95.2 |
| 33 | 6# | 4.5 | 50 | 90 | 9 | 5.6 | 93.3 | 96.9 | 93.3 | 96.9 |
| 34 | 7# | 5.5 | 30 | 110 | 10 | 4.8 | 94.2 | 97.5 | 94.2 | 97.5 |
| 35 | 8# | 6.5 | 10 | 85 | 7.5 | 6 | 95.7 | 93.4 | 95.1 | 94.4 |
| 36 | 9# | 7.5 | 80 | 115 | 8.5 | 4.2 | 92.1 | 97.2 | 92.5 | 96.9 |
| 37 | 10# | 8.5 | 90 | 80 | 5 | 5.4 | 97.3 | 98.0 | 97.2 | 98.0 |
| 38 | 11# | 10 | 5 | 90 | 4 | 4.7 | 96.9 | 93.1 | 97.0 | 93.2 |
| 39 | 12# | 8 | 15 | 70 | 5.5 | 5.8 | 97.3 | 90.9 | 96.8 | 91.5 |
| 40 | 13# | 5 | 25 | 75 | 6 | 5.1 | 96.4 | 91.6 | 96.3 | 91.7 |
| 41 | 14# | 6.5 | 10 | 80 | 4.5 | 4.3 | 95.2 | 91.3 | 95.4 | 91.2 |
| 42 | 15# | 4 | 20 | 90 | 8 | 3.5 | 98.3 | 92.7 | 98.0 | 93.2 |
| 43 | 16# | 2.5 | 25 | 100 | 7 | 4.7 | 92.1 | 95.4 | 93.1 | 94.9 |
| 44 | 17# | 5 | 30 | 95 | 9 | 2.9 | 98.2 | 94.0 | 98.1 | 94.2 |
| 45 | 18# | 6.5 | 25 | 100 | 10 | 3.4 | 96.5 | 97.3 | 96.7 | 97.2 |
| 46 | 19# | 4.5 | 20 | 105 | 7.5 | 4.3 | 93.7 | 94.1 | 93.8 | 94.0 |
| 47 | 20# | 3.5 | 15 | 120 | 8.5 | 5.4 | 94.1 | 93.7 | 94.5 | 93.2 |
| 48 | 21# | 7.5 | 10 | 90 | 5 | 5.1 | 93.5 | 94.8 | 93.2 | 95.0 |
| 49 | 22# | 10 | 5 | 110 | 4 | 4.7 | 94.7 | 95.0 | 95.7 | 94.2 |
| 50 | 23# | 6 | 10 | 85 | 6 | 3.9 | 96.8 | 97.1 | 96.8 | 97.3 |
| 51 | 24# | 4 | 20 | 115 | 8 | 2.1 | 97.6 | 94.9 | 97.9 | 94.6 |
| 52 | 25# | 2 | 75 | 105 | 7 | 5.7 | 95.7 | 97.2 | 95.8 | 97.0 |
| 53 | 26# | 5 | 45 | 90 | 5.5 | 3.3 | 91.3 | 98.4 | 91.5 | 98.3 |
| 54 | 27# | 1 | 100 | 100 | 8 | 2 | 99.2 | 96.3 | 99.0 | 96.5 |

As can be seen from Table 2, different hydrogenolysis catalysts all show good activity and 1,5-pentanediol selectivity in the hydrogenolysis reaction of tetrahydrofurfuryl alcohol, and a high conversion rate can be obtained in a relatively short period of time. In particular, the supporter grafted with a nitrogen-containing ligand provides excellent catalyst stability, and the catalyst activity is substantially maintained after 10 times of reuse.

Examples 55~81: Catalyst Evaluation—Fixed Bed Reactor

The catalyst evaluation of the present invention was carried out in a fixed bed reactor, which was a stainless steel temperature of 150° C., a $H_2$ pressure of 0.3 MPa and a $H_2$ flow rate of 1.5 L/min. After the reduction, the temperature was lowered to the reaction temperature, the hydrogen/catalyst volume space velocity was set at 1000 $h^{-1}$, the flow rate of tetrahydrofurfuryl alcohol aqueous solution was adjusted to the desired mass space velocity of tetrahydrofurfuryl alcohol feed liquid/catalyst, and the pressure was adjusted to the desired reaction pressure. The specific reaction conditions were shown in Table 2. A liquid sample was taken online, and was analyzed using the gas chromatography equipped with a DB-5 capillary column and a flame ionization detector (FID) as described above.

TABLE 3

Reaction conditions and results in the fixed bed reactor

| Examples | Catalyst | The concentration of tetrahydrofurfuryl alcohol (wt %) | Temperature (° C.) | Hydrogen pressure (MPa) | Mass space velocity of tetrahydrofurfuryl alcohol/catalyst ($h^{-1}$) | Results of running 4 hours Conversion rate (%) | Selectivity (%) | Results of running 200 hours Conversion rate (%) | Selectivity (%) |
|---|---|---|---|---|---|---|---|---|---|
| 55 | 1# | 50 | 100 | 5.5 | 2.5 | 92.3 | 95.0 | 92.1 | 95.2 |
| 56 | 2# | 60 | 95 | 6 | 3 | 98.8 | 94.3 | 98.9 | 94.3 |

TABLE 3-continued

Reaction conditions and results in the fixed bed reactor

| Examples | Catalyst | The concentration of tetrahydrofurfuryl alcohol (wt %) | Temperature (° C.) | Hydrogen pressure (MPa) | Mass space veolcity of tetrahydrofurfuryl alcohol/catalyst (h⁻¹) | Results of running 4 hours | | Results of running 200 hours | |
|---|---|---|---|---|---|---|---|---|---|
| | | | | | | Conversion rate (%) | Selectivity (%) | Conversion rate (%) | Selectivity (%) |
| 57 | 3# | 40 | 100 | 4.5 | 2 | 94.5 | 98.1 | 94.6 | 98.0 |
| 58 | 4# | 20 | 105 | 8 | 1.5 | 97.8 | 96.0 | 97.5 | 96.4 |
| 59 | 5# | 70 | 120 | 7 | 1 | 94.0 | 95.3 | 94.2 | 95.5 |
| 60 | 6# | 50 | 90 | 9 | 1.6 | 93.3 | 96.9 | 93.5 | 96.8 |
| 61 | 7# | 30 | 110 | 10 | 1.8 | 94.2 | 97.5 | 94.1 | 97.6 |
| 62 | 8# | 10 | 85 | 7.5 | 2 | 95.7 | 93.4 | 95.4 | 93.5 |
| 63 | 9# | 80 | 115 | 8.5 | 2.2 | 99.2 | 97.2 | 99.0 | 97.4 |
| 64 | 10# | 90 | 80 | 5 | 2.4 | 98.7 | 98.0 | 98.5 | 98.3 |
| 65 | 11# | 5 | 90 | 4 | 2.6 | 96.9 | 93.1 | 97.0 | 93.0 |
| 66 | 12# | 15 | 70 | 5.5 | 2.8 | 97.3 | 92.9 | 97.2 | 92.8 |
| 67 | 13# | 25 | 75 | 6 | 1.1 | 96.4 | 91.6 | 96.5 | 91.8 |
| 68 | 14# | 10 | 80 | 4.5 | 1.3 | 95.2 | 91.3 | 95.6 | 91.1 |
| 69 | 15# | 20 | 90 | 8 | 1.5 | 98.3 | 97.7 | 98.2 | 97.6 |
| 70 | 16# | 25 | 100 | 7 | 1.7 | 92.1 | 95.4 | 92.5 | 95.7 |
| 71 | 17# | 30 | 95 | 9 | 1.9 | 98.2 | 96.9 | 98.4 | 96.8 |
| 72 | 18# | 25 | 100 | 10 | 1.4 | 96.5 | 97.3 | 96.3 | 97.4 |
| 73 | 19# | 20 | 105 | 7.5 | 1.3 | 93.7 | 94.1 | 93.4 | 94.3 |
| 74 | 20# | 15 | 120 | 8.5 | 1.1 | 94.1 | 93.7 | 94.0 | 93.9 |
| 75 | 21# | 10 | 90 | 5 | 1 | 93.5 | 94.8 | 93.2 | 94.5 |
| 76 | 22# | 5 | 110 | 4 | 1.7 | 90.7 | 96.0 | 90.8 | 96.2 |
| 77 | 23# | 10 | 85 | 6 | 1.9 | 96.8 | 97.1 | 96.4 | 97.3 |
| 78 | 24# | 20 | 115 | 8 | 2.1 | 97.6 | 98.5 | 97.7 | 98.4 |
| 79 | 25# | 75 | 105 | 7 | 1.7 | 97.5 | 96.8 | 97.3 | 96.7 |
| 80 | 26# | 45 | 90 | 5.5 | 1.3 | 93.3 | 97.4 | 93.5 | 97.5 |
| 81 | 27# | 100 | 100 | 8 | 2 | 98.5 | 95.2 | 98.7 | 95.3 |

As can be seen from Table 3, in the fixed bed reactor, different hydrogenolysis catalysts also show good activity and 1,5-pentanediol selectivity for the hydrogenolysis reaction of tetrahydrofurfuryl alcohol. And as shown in these 200 hours lifetime tests, the supporter grafted with a nitrogen-containing ligand provides excellent catalyst stability.

Comparative Examples 1~10: Preparation of Polystyrene Supported Catalyst and Silica Gel Supported Catalyst In order to better embody the advantages of the catalysts in the present application, 10 representative catalysts were prepared by directly using polystyrene and silica gel as supporters, which were not grafted with a nitrogen-containing ligand. That is, the metal and the promoter contents, the preparation method and examples were the same as described for the catalysts of 1#, 2#, 10#, 11#, 13#, 19#, 21#, 23#, 26# and 27#, respectively.

TABLE 4

Preparation of comparative catalyst

| Comparative catalyst No. | Noble metal M | Promoter P | Supporter | Content of M (wt %) | M:P (molar ratio) |
|---|---|---|---|---|---|
| 1-1# | Rh | Re | polystyrene | 5 | 1:0.5 |
| 1-2# | Rh | Mo | silica gel | 4 | 1:0.13 |
| 1-10# | Ir | Re | polystyrene | 4 | 1:0.4 |
| 1-11# | Ir | Mo | silica gel | 3 | 1:0.6 |

TABLE 4-continued

Preparation of comparative catalyst

| Comparative catalyst No. | Noble metal M | Promoter P | Supporter | Content of M (wt %) | M:P (molar ratio) |
|---|---|---|---|---|---|
| 1-13# | Ir | V | silica gel | 2.6 | 1:0.8 |
| 1-19# | Pt | Re | silica gel | 4.1 | 1:0.58 |
| 1-21# | Pd | W | silica gel | 3.7 | 1:0.75 |
| 1-23# | Ru | Nb | polystyrene | 2.3 | 1:0.99 |
| 1-26# | Au | Sn | silica gel | 3.9 | 1:0.55 |
| 1-27# | Au | W | silica gel | 9.5 | 1:0.91 |

Comparative Examples 11~20: Performance Evaluation of Polystyrene Supported Catalyst and Silica Gel Supported Catalyst In order to better embody the advantages of catalysts in the present application, catalysts 1-1#~1-10# in the comparative examples were evaluated using the batch reactor, and the evaluation conditions thereof were the same as described for the catalysts 1#, 2#, 10#, 11#, 13#, 19#, 21#, 23#, 26# and 27# in examples 28~54.

TABLE 5

Reaction conditions and results in the batch reactor

| Comparative examples | Catalyst | The amount of catalyst (wt %) | The concentration of tetrahydrofurfuryl alcohol (wt %) | Temperature (° C.) | Pressure (MPa) | Time (h) | The first use Conversion rate (%) | Selectivity (%) | The 10th reuse Conversion rate (%) | Selectivity (%) |
|---|---|---|---|---|---|---|---|---|---|---|
| 11 | 1-1# | 6 | 50 | 100 | 5.5 | 2.5 | 70 | 95.0 | 25 | 86.4 |
| 12 | 1-2# | 7 | 60 | 95 | 6 | 3 | 78 | 94.3 | 28 | 85.7 |
| 13 | 1-10# | 8.5 | 90 | 80 | 5 | 5.4 | 82 | 97.2 | 32 | 87.6 |
| 14 | 1-11# | 10 | 5 | 90 | 4 | 4.7 | 77 | 98 | 37 | 87.1 |
| 15 | 1-13# | 5 | 25 | 75 | 6 | 5.1 | 73 | 90.9 | 23 | 82.3 |
| 16 | 1-19# | 4.5 | 20 | 105 | 7.5 | 4.3 | 67 | 74.1 | 17 | 72.8 |
| 17 | 1-21# | 7.5 | 10 | 90 | 5 | 5.1 | 65 | 69.8 | 16 | 63.4 |
| 18 | 1-23# | 6 | 10 | 85 | 6 | 3.9 | 66.8 | 71 | 19.8 | 75 |
| 19 | 1-26# | 5 | 45 | 90 | 5.5 | 3.3 | 72.1 | 85.4 | 22.1 | 79.2 |
| 20 | 1-27# | 1 | 100 | 100 | 8 | 2 | 76 | 85 | 26 | 72.5 |

As can be seen from Table 5, catalysts, supported directly by polystyrene and silica gel which were not grafted with a nitrogen-containing ligand, were significantly inferior in activity and selectivity to the catalysts prepared in the present application. And their activity decreased rapidly in reuse and their stability was poor.

The above is only preferred embodiments of the present invention, and the scopes of the present invention are not limited thereto; any person skilled in the art would recognize many other variations or alternatives within the technical scopes disclosed in the present invention. Such variations and alternatives are included within the scopes of the invention to be claimed.

The invention claimed is:

1. A catalyst used for preparing 1,5-pentanediol by hydrogenolysis of tetrahydrofurfuryl alcohol, characterized in that: said catalyst comprises a supporter, an active component supported on the supporter, and a promoter supported on the supporter; wherein, the supporter is a polystyrene grafted with a nitrogen-containing ligand; said active component is any one or more of the metal elements Rh, Ir, Pt, Pd, Ru and Au; said promoter is any one or more of the metal elements Re, Mo, W, V, Nb, Ta, Mn, and Sn; wherein the nitrogen-containing ligand in said polystyrene grafted with a nitrogen-containing ligand is any one of imidazole, pyridine, bipyridine and 1,10-phenanthroline.

2. The catalyst according to claim 1, characterized in that: said polystyrene grafted with a nitrogen-containing ligand has the following structural formula:

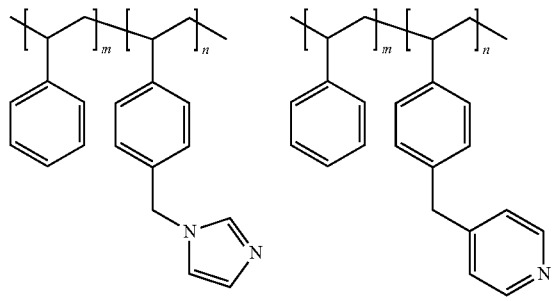

-continued

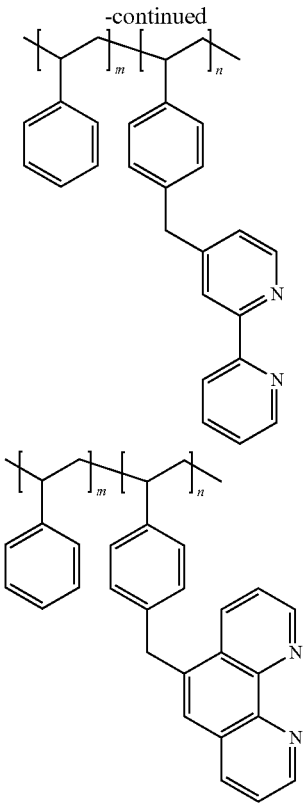

wherein, m=500-2,000, n=200-1,000.

3. The catalyst according to claim 2, wherein m=800-1500 and n=300-800.

4. The catalyst according to claim 2, characterized in that: based on the total weight of the catalyst, said active component is supported in an amount of 0.05-10 wt %; the molar ratio of the active component, the promoter and the nitrogen-containing ligand is 1:(0.01-2):(0.05-4).

5. The catalyst according to claim 4, characterized in that: based on the total weight of the catalyst, said active component is supported in an amount of 1-5 wt %.

6. The catalyst according to claim 4, characterized in that: the molar ratio of the active component, the promoter and the nitrogen-containing ligand is 1:(0.05-1):(0.1-2).

7. The catalyst according to claim 1, characterized in that: based on the total weight of the catalyst, said active component is supported in an amount of 0.05-10 wt %; the molar ratio of the active component, the promoter and the nitrogen-containing ligand is 1:(0.01-2):(0.05-4).

8. The catalyst according to claim 7, characterized in that: based on the total weight of the catalyst, said active component is supported in an amount of 1-5 wt %.

9. The catalyst according to claim 7, characterized in that: the molar ratio of the active component, the promoter and the nitrogen-containing ligand is 1:(0.05-1):(0.1-2).

10. A method for preparing the catalyst according to claim 1, characterized in that: the supporter is added into a soluble salt solution of the active component for isometric impregnation, and then dried at 80-120° C. for 6-24 hours; a soluble salt solution of the promoter is further used for isometric impregnation, and the impregnated supporter is then dried at 80-120° C. for 6-24 hours to obtain the catalyst.

11. The preparation method of the catalyst according to claim 10, characterized in that: the soluble salt of the active component is one or more compounds selected from the group consisting of rhodium chloride, chloroiridic acid, chloroplatinic acid, palladium chloride, ruthenium chloride and chloroauric acid; and the soluble salt of the promoter is one or more compounds selected from the group consisting of ammonium rhenate, ammonium molybdate, ammonium metatungstate, ammonium vanadate, niobiumtartrate, tantalumtartrate, manganese acetate and stannic chloride.

12. A method for preparing 1,5-pentanediol by hydrogenolysis of tetrahydrofurfuryl alcohol using the catalyst according to claim 1, characterized in that: the reaction is carried out in a batch reactor; the mass concentration of the aqueous solution of tetrahydrofurfuryl alcohol is 5-100%; the amount of the catalyst used is 1-10 wt % of the mass of tetrahydrofurfuryl alcohol; the reaction temperature is 50-150° C.; the hydrogen pressure is 1-20 MPa; the reaction time is 2-24 hours; or, the reaction is carried out in a fixed bed reactor; the mass concentration of the aqueous solution of tetrahydrofurfuryl alcohol is 5-100%; the reaction temperature is 50-150° C.; the hydrogen pressure is 1-20 MPa; the mass space velocity of tetrahydrofurfuryl alcohol feed liquid/catalyst in the fix bed reactor is 0.5-4 $h^{-1}$; the volume space velocity of hydrogen/catalyst is 500-1500 $h^{-1}$.

13. The method according to claim 12, characterized in that: the catalyst, before use, needs to be reduced in situ in the presence of hydrogen, and the reduction condition is as follows: the hydrogen pressure is 0.1-1 MPa; for each 100 g of the catalyst, the $H_2$ flow rate is 0.2-10 L/min; the reduction temperature is 50-200° C.; and the reduction time is 1-10 hours.

14. The method according to claim 12, characterized in that: the reaction is carried out in a batch reactor; the reaction temperature is 60-120° C.; the hydrogen pressure is 2-10 MPa; the reaction time is 2-6 hours; or, the reaction is carried out in a fixed bed reactor; the reaction temperature is 60-120° C.; the hydrogen pressure is 2-10 MPa; the mass space velocity of tetrahydrofurfuryl alcohol feed liquid/catalyst in the fix bed reactor is 1-3 $h^{-1}$; the volume space velocity of hydrogen/catalyst is 800-1200 $h^{-1}$.

15. The method according to claim 13, characterized in that: the catalyst, before use, needs to be reduced in situ in the presence of hydrogen, and the reduction condition is as follows: the hydrogen pressure is 0.2-0.4 MPa; for each 100 g of the catalyst, the $H_2$ flow rate is 1-5 L/min; the reduction temperature is 100-180° C.; and the reduction time is 2-6 hours.

* * * * *